United States Patent
Folgerø et al.

(10) Patent No.: US 11,725,969 B2
(45) Date of Patent: Aug. 15, 2023

(54) SAMPLING MODULE FOR MULTIPHASE FLOW METER

(71) Applicant: EQUINOR ENERGY AS, Stavanger (NO)

(72) Inventors: Kjetil Folgerø, Stavanger (NO); Jan Kocbach, Stavanger (NO); Anders Hallanger, Stavanger (NO); Marie Bueie Holstad, Stavanger (NO); Øvind Lystrup, Stavanger (NO); Audun Faanes, Stavanger (NO); Egil Aabel Næsguthe, Stavanger (NO); Eirik Abro, Stavanger (NO); Asbjørn Erdal, Stavanger (NO)

(73) Assignee: EQUINOR ENERGY AS, Stavanger (NO)

( * ) Notice: Subject to any disclaimer, the term of this patent is extended or adjusted under 35 U.S.C. 154(b) by 482 days.

(21) Appl. No.: 16/763,412

(22) PCT Filed: Dec. 13, 2018

(86) PCT No.: PCT/NO2018/050309
§ 371 (c)(1),
(2) Date: May 12, 2020

(87) PCT Pub. No.: WO2019/117729
PCT Pub. Date: Jun. 20, 2019

(65) Prior Publication Data
US 2020/0319005 A1 Oct. 8, 2020

(30) Foreign Application Priority Data
Dec. 13, 2017 (GB) ..................................... 1720750

(51) Int. Cl.
*G01F 1/74* (2006.01)
*G01L 19/00* (2006.01)
(Continued)

(52) U.S. Cl.
CPC ................ *G01F 1/74* (2013.01); *G01F 25/10* (2022.01); *G01L 19/0092* (2013.01);
(Continued)

(58) Field of Classification Search
CPC . G01F 1/74; G01F 25/10; G01F 15/08; G01L 19/0092; G01N 1/2035; G01N 9/24;
(Continued)

(56) References Cited

U.S. PATENT DOCUMENTS 5,394,339 A * 2/1995 Jones ........................ G01F 1/58
702/50
6,212,948 B1 4/2001 Ekdahl et al.
(Continued)

FOREIGN PATENT DOCUMENTS

| CN | 102405398 | 4/2012 |
| CN | 103132995 | 6/2013 |

(Continued)

OTHER PUBLICATIONS

International Search Report and Written Opinion of the International Searching Authority dated Mar. 8, 2019 in International (PCT) Application No. PCT/NO2018/050309.
(Continued)

*Primary Examiner* — Eric S. McCall
*Assistant Examiner* — Timothy P Graves
(74) *Attorney, Agent, or Firm* — Wenderoth, Lind & Ponack, L.L.P.

(57) ABSTRACT

A sampling module is for mounting in a pipeline with a multiphase flow meter and for receiving multiphase fluid from the pipeline. The sampling module includes: a separation chamber for receiving and separating a sample volume of fluid from the multiphase fluid, the separation chamber having a vertical extent when in use; a lower valve for opening and closing a lower fluid path between a lower
(Continued)

end of the separation chamber and the pipeline; an upper valve for opening and closing an upper fluid path between an upper end of the separation chamber and the pipeline; a lower sensor for measuring fluid properties of the fluid in a lower part of the separation chamber; and an upper sensor for measuring fluid properties of the fluid in an upper part of the separation chamber.

34 Claims, 2 Drawing Sheets

(51) Int. Cl.
*G01N 1/20* (2006.01)
*G01N 33/28* (2006.01)
*G01F 25/10* (2022.01)
*G01N 9/24* (2006.01)
*G01N 27/06* (2006.01)

(52) U.S. Cl.
CPC .............. *G01N 1/2035* (2013.01); *G01N 9/24* (2013.01); *G01N 27/06* (2013.01); *G01N 33/2823* (2013.01); *G01N 2001/205* (2013.01)

(58) Field of Classification Search
CPC ............... G01N 27/06; G01N 33/2823; G01N 2001/205; G01N 33/241; G01N 33/246; G01N 9/00; G01N 9/36; G01N 27/02; G01N 27/04; G01N 27/22; G01N 27/221
See application file for complete search history.

(56) References Cited

U.S. PATENT DOCUMENTS

| 6,454,002 | B1 | 9/2002 | Stokes et al. |
| 2008/0015792 | A1 | 1/2008 | Scott |
| 2012/0111571 | A1* | 5/2012 | Eriksen .................. G01N 33/18 |
| | | | 166/336 |
| 2012/0210768 | A1 | 8/2012 | Hurmuzlu et al. |
| 2014/0366653 | A1 | 12/2014 | Husveg |
| 2015/0007648 | A1* | 1/2015 | Theron .................. G01N 33/28 |
| | | | 73/152.23 |

FOREIGN PATENT DOCUMENTS

| EP | 0 213 838 | 3/1987 |
| GB | 2 406 386 | 3/2005 |
| GB | 2538610 | 11/2016 |
| GB | 2562993 | 12/2018 |
| WO | 2016/094474 | 6/2016 |
| WO | 2016/161358 | 10/2016 |
| WO | 2017/091522 | 6/2017 |
| WO | 2018/160927 | 9/2018 |

OTHER PUBLICATIONS

GB Search Report dated Mar. 26, 2018 in GB Application No. 1720750.7.
Extended European Search Report dated Jul. 28, 2021 in European Patent Application No. 18888538.8.
First Office Action dated Feb. 16, 2023 in Chinese Patent Application No. 201880080435.8.

* cited by examiner

SAMPLING MODULE FOR MULTIPHASE FLOW METER

BACKGROUND OF THE INVENTION

1. Field of the Invention

The invention relates to a sampling module for mounting in a pipe with a multiphase flow meter and for receiving multiphase fluid from the pipeline as well as to a method using the sampling module for obtaining input parameters for a multiphase flow meter. In some example implementations the sampling module and the multiphase flow meter are in a subsea location and the pipeline is a pipeline of a subsea installation.

2. Description of the Related Art

In the oil and gas industry, amongst other industries, there is a need to obtain information regarding multiphase fluids. Multiphase flow meters are used extensively in the oil and gas industry for allocation purposes and production optimization and they are particularly important for measurement of subsea tie-ins. The flow rates provided by a multiphase flow meter are calculated from a combination of measurements, typically electromagnetic, nucleonic and differential pressure measurements. To achieve the specifications, multiphase flow meters rely on accurate knowledge fluid properties, such as the permittivity and attenuation coefficients for the oil, gas and water in the multiphase fluid, along with accurate inputs for pressure and temperature. The salinity or conductivity of water in the multiphase fluid is also required, although this may also be measured with dedicated sensors in some multiphase flow meters. The accuracy of a multiphase flow meter relies on the accuracy of the input parameters. The multiphase flow meter use algorithms supplied with appropriate input parameters in order to calculate measurements of the multiphase flow. It can therefore be important to have a system for keeping the input data to multiphase flow meter and/or the algorithms updated with any changes to the fluid properties that are being measured.

Multiphase flow meters are often used with subsea installations and the multiphase fluids that are passed through such subsea installations, which may for example be production fluids from an oil field. It will be appreciated that there are challenges connected with this, due to the location of the subsea installation and since the fluids concerned are naturally produced fluids with unpredictable characteristics. For effective monitoring it is necessary to carry out multiphase measurements before comingling the production from many wells, and this hence requires multiphase flow meters to be mounted in remote locations below the surface of the sea. In this context there are even greater challenges associated with calibration of the multiphase flow meters and ensuring accuracy of the input parameters used to determine the measurements of the multiphase fluid.

SUMMARY OF THE INVENTION

Viewed from a first aspect, the invention provides a sampling module for mounting in a pipeline with a multiphase flow meter and for receiving multiphase fluid from the pipeline, wherein the sampling module comprises: a separation chamber for receiving and separating a sample volume of fluid from the multiphase fluid, the separation chamber having a vertical extent when in use; a lower valve for opening and closing a fluid path between a lower end of the separation chamber and the pipeline; an upper valve for opening and closing a fluid path between an upper end of the separation chamber and the pipeline; a lower sensor for measuring fluid properties of the fluid in a lower part of the separation chamber; and an upper sensor for measuring fluid properties of the fluid in an upper part of the separation chamber; wherein the sample module includes a controller for opening and closing the valves in each one of the following operations: opening and closing both the lower valve and the upper valve together; opening and closing the upper valve whilst the lower valve remains closed; and opening and closing the lower valve while the upper valve remains closed.

With this sampling module a sample volume of multiphase fluid from the pipeline can be received in the separation chamber with one or both valves open, and then held within the separation chamber until the sample volume has separated. The upper and lower sensors are then able to measure properties at different parts of the separation chamber in order to measure the properties of different parts of the fluid after separation. This allows for an analysis of the multiphase fluid after separation to obtain parameters of the constituent parts of the multiphase fluid. The results of this analysis can then be used to maintain or improve the accuracy of the multiphase flow meter, for example by calibration or re-calibration of the multiphase flow meter and/or by updating input parameters used by the multiphase flow meter. This process may advantageously be carried out in parallel with on-going flow of the fluid through the pipeline and/or through the multiphase flow meter, for example via fitting the sampling module in a by-pass or parallel flow line as discussed below so that sampling does not stop the flow through the multiphase flow meter. The sampling module can be used periodically to identify any variations in the multiphase fluid over time and/or used in reaction to upstream changes, such as changes to production parameters, in order to ensure that resultant changes in the make-up of the multiphase fluid are taken account of and accuracy of the multiphase flow meter can be maintained. In this way the sampling module can provide for in-line calibration of the multiphase flow meter, for example by allowing the multiphase flow meter settings or input data to be updated in reaction to changes in the parameters of the fluid measured by the sampling module.

The multiphase fluid may be fluid from an oil and gas installation, such as a mixture comprising two or more of gaseous hydrocarbons, liquid hydrocarbons and water. Thus, the pipeline may be an oil and gas pipeline connected to an oil and gas installation.

This sampling module can be used in a subsea installation and thus it may be a subsea sampling module for receiving fluid from a subsea well or pipeline. In that case the multiphase flow meter is a subsea multiphase flow meter. It will be appreciated that ensuring the accuracy of subsea multiphase flow meters is a significant challenge due to difficulties in accessing the subsea location to take samples for the purpose of calibration and/or confirming the accuracy of subsea multiphase flow meters. There are hence significant advantages in using the proposed sampling module for subsea installations since it permits on-going updates to the parameters used by the multiphase flow meter without the need for any intervention at the subsea location of the multiphase flow meter.

To receive the sample volume the separation chamber is opened via one or both of the valves for a period of time. The valves can then be closed with a settling time allowed in order to hold the sample volume within the separation chamber and allow it to settle. As the separation chamber has a vertical extent then the lighter constituents of the multiphase fluid will move to the upper part of the chamber, and the heavier constituents of the multiphase fluid will move to the lower part of the chamber. Depending on the fluid that has entered the chamber this can result in gaseous or liquid hydrocarbons at the upper part of the chamber adjacent the upper sensor, and liquid hydrocarbons or water at the lower part of the chamber adjacent the lower sensor. The upper sensor and the lower sensor can hence be used to measure different constituent parts of the multiphase fluid, typically via measurements of a single phase of the multiphase fluid.

In order to obtain a sample volume of the multiphase fluid as a complete mixture the sampling module may be arranged to open both the lower valve and the upper valve so that multiphase fluid from the pipeline flows through the sampling module, and to then close both valves to retain a sample volume of the multiphase fluid in the separation chamber. When this fluid has settled within the vertical extent of the separation chamber then it will separate into the constituent parts of the multiphase fluid.

Often there will be three phases (i.e. gaseous hydrocarbons, liquid hydrocarbons and water) in the multiphase fluid. To provide accurate input information to a multiphase flow meter it is required to know parameters concerned with each phase. With the proposed use of two sensors then only two phases can be measured for each sample. It is possible to add more sensors at different levels in order to allow for a finer resolution along the vertical extent of the separation chamber, but this adds costs and complexity. It is beneficial to be able to sample only the heavier part or only the lighter part of the multiphase fluid in order to find parameters concerned with all three phases.

In order to obtain a sample volume of just the heavier parts of the multiphase fluid the sampling module may be arranged to open the upper valve whilst the lower valve remains closed. Heavier parts of the multiphase fluid, such as liquid parts of the multiphase fluid, may then enter the sample volume displacing any lighter phases, which rise to the top of the chamber and may exit the open upper valve. These heavier parts can become trapped within the separation chamber so that the sample volume of fluid from the multiphase fluid includes mainly the heavier phases. The upper valve can then be closed with separation time being allowed before measurements are taken with the upper sensor and lower sensor. This can allow for measurements focused on heavier parts, which may include separation of the heavier parts into the upper part and lower part of the separation chamber, such as separation of liquid hydrocarbons from water.

It is also possible to obtain a sample volume of the lighter parts of the multiphase fluid. In order to do this, the sampling module may be arranged to open the lower valve whilst the upper valve remains closed. Lighter parts of the multiphase fluid, such as gaseous parts of the multiphase fluid may then enter the sample volume displacing any heavier phases, and these lighter parts can become trapped within the separation chamber so that the sample volume of fluid from the multiphase fluid includes mainly the lighter parts. The lower valve can then be closed with separation time being allowed before measurements are taken with the upper sensor and lower sensor. This can allow for measurements focused on lighter phases, which may include separation of lighter parts into the upper part and heavier parts into the lower part of the separation chamber, such as separation of gaseous hydrocarbons from lighter liquid hydrocarbons.

The sampling module may include a controller for controlling operation of the sampling module. The controller may be arranged to control the sequence and timing of valve opening and closing operations. For example, the controller may be arranged to control the lower valve and upper valve as discussed above in order to open and close to obtain a sample volume of the multiphase fluid as a whole, the heavier parts of the multiphase fluid, or the lighter parts of the multiphase fluid. The controller may be arranged to open the required valve(s) for a preset period of time to allow for the required fluid to fill the separation chamber. This preset period of time may include a time allowed to flush out fluid already present in the separation chamber. In the case where only the lighter parts or only the heavier parts are to be included in the sample volume, i.e. where the sample volume fills the chamber with only one valve open, then the controller may open both valves for a period of time initially in order to ensure that the separation chamber is fully flushed with the multiphase fluid.

Where the sample volume is to include only the lighter or heavier parts of fluid then some separation may occur as the fluid is gathered with the lower or upper valve open and the other valve closed. Thus, the upper sensor and the lower sensor may be able to detect the presence of a separated phase, such as a purely gaseous phase or a purely liquid phase (of water and/or of hydrocarbons). In that case the time allowed to fill the separation chamber before it is sealed for settling of the sample volume may be varied depending on readings from the sensor(s).

The controller may be arranged to allow for a settling time after both valves are closed in order that the sample volume can fully separate within the vertical extent of the separation chamber. The settling time may be a pre-set time, or it may be a time that varies depending on readings from one or both of the upper sensor and/or the lower sensor. In the latter case the controller may monitor the upper sensor and/or the lower sensor with the settling time deemed to be completed when the measurements from one of or both of the sensors shows a single phase in the respective part of the separation chamber.

In some examples the controller may use the upper or lower sensors, or other sensors such as level sensors, to determine if an unwanted phase is present after settling of the fluid. For example, the controller may check for gas phase at the level of the upper sensor after the upper valve is closed in cases where it is desired to measure a liquid phase with the upper sensor. In the case that unwanted gas is detected then the controller may be arranged to re-open the upper valve to release the gas and displace it with new multiphase fluid. This can then be re-settled to allow for a greater amount of liquid and a lesser amount of gas after re-settling.

The separation chamber has a vertical extent when it is installed and in use, and this vertical extent in example embodiments is the total distance between the lower valve at the lower end and the upper valve at the upper end. The upper part of the separation chamber may for example be the upper 50% of the vertical extent of the separation chamber, and the lower part may hence be the lower 50% of the vertical extent of the separation chamber. The upper sensor is within the upper part of the separation chamber and is ideally spaced apart from the lower sensor in the lower part of the separation chamber by at least 20% of the total extent of the separation chamber, for example it may be spaced apart by at least 30% of the total extent of the separation chamber or by at least 40% of the total extent of the separation chamber. Whilst a greater spacing between the sensors may increase the likelihood of having separate phases at each sensor it may also be necessary to allow a relatively large spacing between the lower or upper valve and the respective lower or upper sensor. For example, there may be a need to avoid the sensor being too close to the valve to avoid any effect of the valve on the measurements of the sensor and/or to allow for space for fittings between the valve, the associated valve pathways, and other parts of the sampling module that make up the separation chamber. In some examples the spacing between the lower valve or the upper valve and the respective lower sensor or upper sensor may be 15-35% of the total vertical extent of the separation chamber (i.e. the total distance between the valves).

The separation chamber may take the form of an elongate vertical chamber between the lower valve and the upper valve, with the valves placed at the extreme ends of the chamber. This may be a tube-like chamber, such as a tube with a circular construction. In order to allow for a suitable measurement then the width of the tube (i.e. diameter for a circular tube) adjacent the sensors may be at least 50 mm, such as a tube with width in the range 50-150 mm, or optionally a tube of width in the range 50-100 mm. In one example the tube adjacent the sensors is a 3 inch pipe (i.e. a diameter of about 76.2 mm). It is not essential that the width of the separation chamber is constant along its full extent and so the width may vary, for example there may be a smaller width section such as a smaller diameter tube at the outer ends of the separation chamber adjacent to the valves.

In the case of a separation chamber comprising a tube of width in the range 50-100 mm adjacent the sensors then the total vertical extent of the separation chamber may be in the range 800-1600 mm, such as a vertical extent of 900-1400 mm. This has been found to provide sufficient space for clear separation of phases and for the upper and lower sensors to be spaced apart widely enough to obtain useful measurements for a range of water in liquid (WLR) ratios.

The lower valve and the upper valve may each be in a valve housing. The valve housings may for example allow for connection to the pipeline via a T-connector or other suitable joint. The two valve housings may be coupled to a central part of the sampling module to form the separation chamber, and the central part of the sampling module may include the upper sensor and the lower sensor. One arrangement may use a modular construction where the central part is mechanically coupled to the valve housings such as via flanges and bolts or screws. In an alternative arrangement the central part and the valve housings may be formed integrally with one another or welded together. The latter arrangement can allow for a smaller spacing between the valve and the sensors, which may then allow for the total vertical extent of the sampling module to be reduced.

The upper sensor and the lower sensor may each be a single sensor or they may be provided by an upper sensor set and a lower sensor set. The upper sensor set and the lower sensor set may each comprise one or more of: a densitometer such as a gamma densitometer; a permittivity sensor; and/or a conductivity sensor. In some examples the upper sensor is provided by an upper sensor set comprising a densitometer and a permittivity sensor. The lower sensor may be provided by a lower sensor set comprising a densitometer and a permittivity sensor as well as optionally a conductivity sensor. The permittivity sensor and the conductivity sensor may be combined as a single sensor.

The densitometer may be any suitable sensor for measurement of the density of the fluid, such as a gamma densitometer or an ultrasonic transducer. The sensor may be similar to densitometers used in multiphase flow meters for measuring the density of the multiphase fluid. In the case of a gamma densitometer the sensor may determine an estimate of the density by measurement of the linear attenuation of gamma rays. Measurement of the density of a single phase of the multiphase fluid allows for increased accuracy in measurements made via the multiphase flow meter, especially if the density of each phase can be found. Thus, it is advantageous for both the upper sensor set and the lower sensor set to include a densitometer.

The permittivity sensor may measure the dielectric constant of the fluid to determine various properties of the fluid depending on the phase in question. The dielectric constant for oil varies with density and with the polarizability of the oil. For water the dielectric constant varies with salinity and temperature. In the case of gaseous hydrocarbons the dielectric constant mainly varies with density changes. Multiphase flow meters often take a permittivity measurement for the multiphase fluid and therefore the accuracy of information from the multiphase flow meter can be increased by having details of the dielectric constants for each phase of the multiphase fluid.

Measurement of conductivity is of primary interest for the water within the multiphase fluid. Conductivity of the water varies with salinity, ion composition and temperature. In some examples the conductivity is measured along with permittivity, such as by use of a sensor that measures the complex permittivity, where conductivity may be obtained from the imaginary part of the complex permittivity. Conductivity may also be measured via a resistivity/conductivity measurement between electrodes, via attenuation of microwaves, or via inductive/eddy current measurement techniques, for example.

The sampling module may include further sensors in addition to the upper sensor set and lower sensor set, such as one or more of a temperature sensor, a pressure sensor, level detectors, emulsion characterization sensors, ultrasonic transducers and/or a viscosity meter. Temperature and pressure sensors may advantageously be included to confirm that the sample volume is at the same temperature and pressure as the multiphase fluid at the multiphase flow meter. This ensures that the parameters provided from the sampling module will have the desired effect in maintaining or increasing the accuracy of the measurements from the multiphase flow meter. Temperature and pressure may also be required in order to determine the correct output parameters from other sensors, such as from the densitometer, permittivity sensor and conductivity sensor. Level measurement and/or emulsion characterization sensors can be used to find the interface between phases and/or to confirm when separation has progressed sufficiently for useful measurements to be made. In the case of measurement of all phases of the multiphase fluid then level measurement may be used to find the WLR by determining the relative volume of water and hydrocarbon liquids. Ultrasonic transducers may be used to determine the velocity of sound through the fluid, which can aid in relation to density measurements and for determining the calorific value of hydrocarbon gas. Information on viscosity may be used to improve the accuracy of the multiphase flow meters by adding more information on flow characteristics of the multiphase fluid.

The sampling module may include a connection to a source of hydrate blocker for supplying hydrate blocker to the separation chamber before it is closed off in periods when it is not in use. The hydrate blocker may be monoethylene glycol (MEG), for example. Whilst the separation chamber could simply be filled with fluid from the pipeline and then sealed this creates a risk of hydrate formation within the separation chamber. The use of a hydrate blocker to prevent fouling of the separation chamber can therefore be beneficial. The separation chamber may be provided with a hydrate blocker by opening the upper valve and supplying hydrate blocker to the separation chamber to displace the fluid in the chamber. When sufficient hydrate blocker has been introduced then the upper valve can be closed and the sampling module can be left unused for a long period of time if necessary.

The separation chamber may be a corrosion resistant material such as stainless steel. Alternatively or additionally, the interior of the separation chamber may be coated or lined to reduce the risk of corrosion or fouling such as hydrates or scale formation. This can avoid the need for hydrate blocker in some circumstances, which simplifies the sampling module as a connection to a MEG line or similar is no longer needed.

In some examples the separation chamber may be heated via a heater such as an electrical heater. Heating of the separation chamber may be used during measurement if the temperature within the separation chamber would otherwise drop below the temperature of the multiphase fluid in the multiphase flow meter. Heating of the separation chamber may be used when the sampling module is not taking measurements in order to maintain a minimum temperature to reduce the risk of hydrate formation. The controller may be arranged to control the heater so that the temperature of the fluid within the separation chamber does not drop below such a minimum temperature and/or does not drop below the temperature of the multiphase fluid in the multiphase flow meter. An alternative to heater could be to insulate the separation chamber, and also to install the separator chamber close to the multiphase meter and within the same insulation such that the separator chamber is heated by the multiphase meter.

As will be appreciated from the above the sampling module has advantages when used subsea and in particular when used subsea with a subsea multiphase flow meter. The invention extends to a combination of the sampling module and a multiphase flow meter, for example where the sampling module and the multiphase flow meter are mounted in parallel to the same subsea pipeline. Thus, in another aspect the invention provides a multiphase flow meter apparatus comprising: a multiphase flow meter for monitoring fluid flows in a pipeline; and a sampling module as described above.

The separator chamber is intended to be installed in parallel to the pipe where the main production will flow. In order to get a flow into the separator chamber despite the reduced diameter, it may be beneficial or necessary to include a restriction in the main pipe. There is most often a pressure drop across multiphase meters. Thus, by installing the separator chamber in parallel to the multiphase meter, then the multiphase meter can provide the required restriction effect and there is no need to introduce any additional restriction or pressure drop. Similar the separation chamber needs to be installed in a vertical extent. The multiphase meter also has a vertical orientation and combining the two avoids the need for an extra vertical section. There may be a controller for adjustment of the multiphase flow meter in reaction to measurements from the sensors of the sampling module. A single controller may be provided to control both of the sampling module, as discussed above, and the multiphase flow meter. The multiphase flow meter may include an algorithm that determines output values of the multiphase flow meter based on measurements of the multiphase fluid. This algorithm may use parameters measured by the sampling module as input parameters or variables such that the output values of the multiphase flow meter may be calculated taking account of any changes in the composition of the multiphase fluid as measured via the sampling module.

The sampling module may be coupled to the pipeline in parallel with the multiphase flow meter, for example in a by-pass adjacent to the multiphase flow meter. The lower and upper valves of the sampling module may be coupled to the pipeline via T-connectors.

In a yet further aspect the invention provides a method for obtaining input parameters for a multiphase flow meter, the method comprising using a sampling module as described above. Thus, the method may use a sampling module for mounting in a pipeline with the multiphase flow meter and for receiving multiphase fluid from the pipeline, wherein the sample module includes a lower valve, an upper valve, and a controller for opening and closing the valves in each one of the following operations: opening and closing both the lower valve and the upper valve together; opening and closing the upper valve whilst the lower valve remains closed; and opening and closing the lower valve while the upper valve remains closed, wherein the method comprises: opening and closing at least one of a lower valve and an upper valve of the sampling module in order to allow fluid flow along a fluid path between a lower end of the separation chamber and the pipeline and/or between an upper end of the separation chamber and the pipeline; thereby obtaining a sample volume of fluid from the multiphase fluid in a separation chamber of the sampling module, the separation chamber having a vertical extent when in use; closing the lower valve and the upper valve; holding the sample volume within the separation chamber to allow the fluid to settle and separate; measuring fluid properties of the settled fluid in a lower part of the separation chamber using a lower sensor in the lower part of the separation chamber; and measuring fluid properties of the settled fluid in an upper part of the separation chamber using an upper sensor in the upper part of the separation chamber.

The method may include using the sampling module as described above in relation to optional features for the first aspect. The method may include using the measured fluid properties for an analysis of the multiphase fluid after separation to obtain parameters of the constituent parts of the multiphase fluid. The results of this analysis may then be used to maintain or improve the accuracy of the multiphase flow meter, for example the method may include calibration or re-calibration of the multiphase flow meter and/or updating input parameters used by the multiphase flow meter. This process may be carried out in parallel with on-going flow of the fluid through the pipeline and/or through the multiphase flow meter. The method may hence include in-line calibration of the multiphase flow meter, for example by allowing the multiphase flow meter settings or algorithms to be updated in reaction to changes in the parameters of the fluid measured by the sampling module used in a periodic sampling regime.

The method may be a method for obtaining input parameters for a subsea multiphase flow meter wherein the sampling module is a subsea sampling module and the pipeline is a subsea pipeline. Thus, the fluid handling and measurement steps of the method may be carried out in a subsea location. With an appropriate controller and/or data processing equipment, such as a computer device, also being provided subsea then the entirety of the method may be carried out in the subsea location, without any need for transmission of data to a topside location. However, since the multiphase flow meter may itself be provided with a means to communicate with a topside installation then the analysis of the measurements in the method may occur at such a topside installation, i.e. the measurements from the sampling module may be transmitted to the topside installation for analysis and updates to the multiphase flow meter may be transmitted from the topside installation after the analysis.

The method can include controlling the upper and lower valves in a specified sequence with suitable timing as described above in order to obtain a required sample of fluid from the multiphase fluid. A settling time may be used, as discussed above, to allow for separation of the fluid within the separation chamber, and the method may include using the upper or lower sensors, or other sensors such as level sensors, to determine if settling has been completed and/or if an unwanted phase is present after settling of the fluid.

A hydrate blocker, such as MEG as described above, may be used to prevent fouling of the separation chamber. The method may include providing a hydrate blocker to the separation chamber via a hydrate blocker supply line with the upper valve open so that the hydrate blocker displaces the fluid in the separation chamber. When sufficient hydrate blocker has been introduced then the upper valve may be closed.

Heating of the separation chamber may be used during measurement if the temperature within the separation chamber would otherwise drop below the temperature of the multiphase fluid in the multiphase flow meter. Heating of the separation chamber may be used when the sampling module is not taking measurements in order to maintain a minimum temperature to reduce the risk of hydrate formation. The method may include using a heater such as an electrical heater, and optionally controlling the heater with a controller of the sampling module.

An alternative to heating could be to insulate the separation chamber, and also to install the separator chamber close to the multiphase meter and within the same insulation such that the separator chamber is heated by the multiphase meter.

In a further aspect, the invention provides a computer program product for carrying out the method of the invention. This may be a control algorithm for the sampling module, for example. Thus, the invention may provide a computer program product for obtaining input parameters for a multiphase flow meter, the computer program product comprising instructions that when executed will control a sampling module as described above in order to operate it in accordance with the method set out above.

BRIEF DESCRIPTION OF THE DRAWINGS

A preferred embodiment of the invention will now be described by way of example only and with reference to the accompanying figures in which.

DETAILED DESCRIPTION OF THE INVENTION

Figure 1:
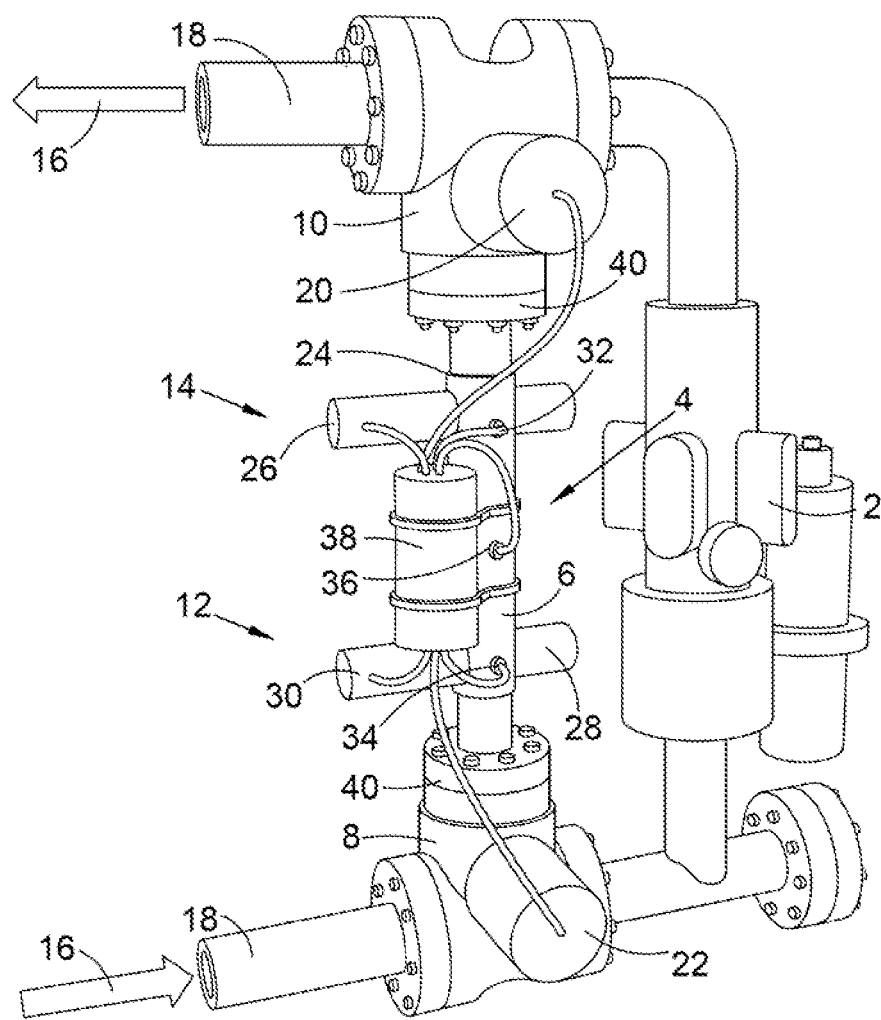
FIG. 1 shows a sampling module and a multiphase flow meter 2 mounted in parallel to a pipe.
Figure 2:
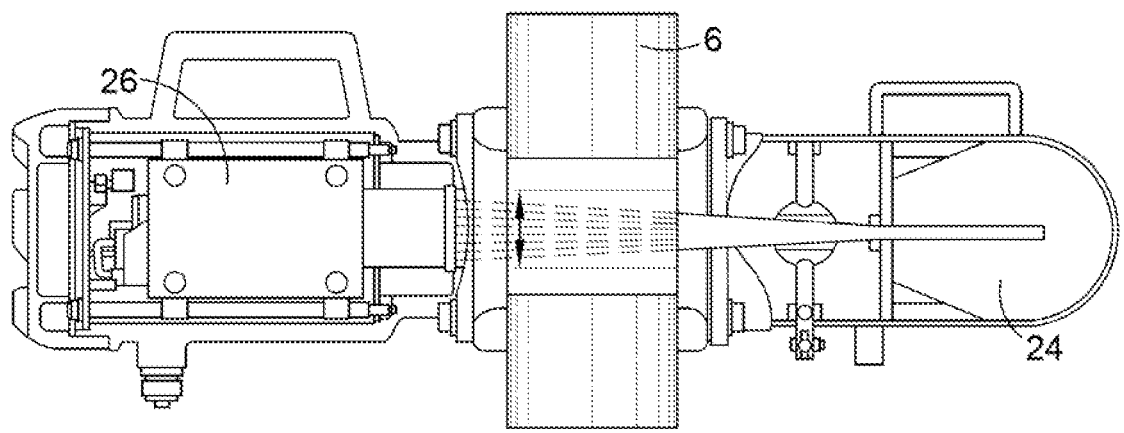
FIG. 2 is an enlarged cross-section of a densitometer arrangement used in the sampling module of FIG. 1.

As shown in the example of FIG. 1 a sampling module 4 is provided in a pipeline 18 in parallel with a multiphase flow meter 2. The flow rates provided by the multiphase flow meter 2 are based on measurements of such as for example permittivities, linear attenuation coefficients and differential pressure across a Venturi tube. To achieve the specifications provided by vendors, multiphase flow meters 2 rely on accurate knowledge of fluid properties as illustrated in FIG. 2. The main input parameters for a typical multiphase flow meter 2 are water conductivity, linear attenuation constants and permittivity for oil, gas and water at operating conditions. Uncertainties or errors in the input parameters can result in large uncertainties in the outputs of the multiphase flow meter 2. Thus, it is of vital importance that the input parameters are known with high accuracy.

It is proposed to use a sampling module 4 such as that shown in FIG. 1 in order to provide accurate input parameters based on measurements of multiphase fluid 16 taken from the same pipeline 18 to which the multiphase flow meter 2 is mounted. With this approach fluid samples of the actual multiphase flow are characterized. Thus, the analysis is done on representative fluids. Also, all parameters are measured at actual operating conditions, for example at subsea temperature and pressure. The proposed sampling module 4 comprises a separation chamber 6 which is a vertical tube-like space between a lower valve 8 and an upper valve 10. The valves 8, 10 can be mounted to the pipeline 18 via T-connectors. The fluid within the separation chamber 6 can be measured using a lower sensor set 12 in a lower part of the chamber and an upper sensor set 14 in an upper part of the chamber. These sensor sets 12, 14 may comprise various sensors as discussed below. In the example of FIG. 1 the upper sensor set 14 comprises a gamma densitometer with a gamma source 24 and gamma detector 26, as well as a permittivity sensor 32. The lower sensor set 12 comprises a gamma densitometer with a gamma source 28 and a gamma detector 30, as well as a combined permittivity and conductivity sensor 34. The sample module 4 also has temperature and pressure sensors 36. A controller 38 in the form of an electronics module 38 is used to control opening and closing of the valves 8, 10 and measurements taken by the various sensors. The valves are opened and closed by an upper valve actuator 20 and a lower valve actuator 22.

The primary input parameters for the multiphase flow meter 2 can be measured directly via the sampling module 4 with similar (or identical) instrumentation to that in the multiphase flow meter 2. Thus, uncertainty due to PVT estimation and correlations between densities and primary multiphase flow meter 2 input parameters are avoided. Compared to sampling methods where subsea multiphase samples are taken with ROV followed by chemical analysis in topside laboratory to determine hydrocarbon composition, the sampling module 4 has a very short response time from sampling to completed analysis. The operational cost is also heavily reduced compared to the use of ROV. Additional information useful in relation to multiphase flow meter 2 measurements, e.g. for redundancy, can also be estimated by the sampling module 4 by the use of suitable sensors. Examples include estimation of water liquid ratio (WLR) by adding level detectors, viscosity sensors, and so on, as discussed further below.

There are also additional advantages of the sampling module 4 apart from increasing the reliability of multiphase flow meters 2. Characterization of fluid parameters is of importance for flow assurance and production optimization. Examples include characterization of water for hydrate, corrosion and scale control.

The sampling module 4 is placed close to the multiphase flow meter 2 to ensure that the operating conditions are as equal as possible. In this example the sampling module 4 is placed directly in parallel with the multiphase flow meter 2. Input data is transmitted from the controller 38 to the multiphase flow meter 2 where it is used to update the multiphase flow meter 2 with any changes required, for example for input parameters in an algorithm of the multiphase flow meter 2. The controller 38 for the sampling module 4 could be combined in the same hardware/software as an electronic module for the multiphase flow meter 2 or a subsea control module During normal operation of the pipeline 18 and the multiphase flow meter 2 the separation chamber 6 is filled with a hydrate blocker such as MEG, both the valves 8, 10 are closed and all the multiphase flow 16 is routed through the multiphase flow meter 2. When a new characterization of the multiphase fluid is needed (for example, if upstream conditions change or at a periodic time) then some of the flow 16 is routed through the sampling module 4 and analyzed.

In one example, the operation is carried out as follows. First, both valves are opened and some of the multiphase flow 16 will go through the separation chamber 6 ensuring that the separation chamber 6 is filled with representative process fluids. This flushing will also ensure that the separation chamber 6 is heated to the process temperature. The upper valve 10 can be closed when process fluids have replaced the old fluid and this can be indicated by the outer wall temperature reaching the process temperature. Gas will then start to accumulate whereas liquid is displaced by the gas and falls towards the bottom of the separation chamber 6. The lower valve 8 is then closed, which may be after a certain time or may be when the upper sensors 14 detect only gas in the upper part of the separation chamber 6. The gas is then analyzed by the upper sensors 14.

After this first analysis the upper valve 10 is opened to release the gas and to allow liquid to accumulate and gradually fill the separation chamber 6. Optionally, if the wall temperature has decreased significantly below process temperature, then the separation chamber may be flushed with process fluid again by opening both valves in order to stabilize temperature. With the lower valve 8 closed the upper valve 10 is closed when gas has been displaced by liquid in front of the upper sensors 14. Oil and water are then allowed to separate and stabilize, resulting in an oil layer in front of the upper sensors 14 and water in front of the lower sensors 12. Oil is hence characterized by the upper sensors 14 and water by the lower sensors 12.

Trapped gas that is separated from the liquid will rise to the top of the separation chamber 6, and may make up a gas pocket in front of the upper sensors 14. This is easily detected by the sensors 14. If required then the upper valve 10 can be re-opened to release the gas and to sample more liquid. This might also be needed if the liquid flow rate into the separation chamber 6 is so high that it is it is difficult for the upper sensors 14 to detect when the liquid level has increased to cover the sensors 14. The upper valve can then be closed or regulated to reduce the flow rate such that the phase of the fluid in front of the upper sensors can be identified. If the WLR is low, the lower sensors may see oil and not water.

Other sequences of valve opening and closing are possible. For example, both valves 8, 10 may be open to flush the separation chamber 6 and then both valves may be closed to capture a sample of the entirety of the multiphase fluid. Level sensors might then be used to determine the gas fraction.

The flow of fluid into the separation chamber is enhanced by the pressure restriction in the multiphase meter. This is an advantage of mounting the separation chamber in parallel to the multiphase meter.

The flushing of the separation chamber 6 should ideally be sufficient to exchange all of the existing content of the separation chamber 6 with a new sample. The filling time of the separation chamber 6 will depend on flow rates and gas volume fraction as well as the size and geometry of the sampling module 4. The filling times for typical flow conditions can be determined experimentally or via modelling, and optimal operating ranges for given dimensions can then be determined. CFD simulations of a typical two-phase flow with 50% gas volume fraction (GVF) indicate that a sampling time of 30 seconds will generally be sufficient to fill the separation chamber 6 with liquid and sufficient amounts of gas.

Data from the upper and lower sensors 12, 14 are recorded and stored when their signals show stable readings (indicating that separation of oil and water is completed)

The liquid in the separation chamber 6 is replaced by a hydrate blocker such as MEG when the liquid analysis is completed. This is done by opening the upper valve 10, and adding MEG to the lower part of the separation chamber 6 (i.e. to the water phase). MEG will then displace the liquid from the separation chamber 6. MEG will mix with water and gradually the concentration of MEG will increase above a level that is safe for storage. The upper valve 10 can then be closed.

The optimal placement of the sampling module 4 is directly in parallel with the multiphase flow meter 2 at the flow control module as illustrated in FIG. 1. This implies some restrictions to the pipe routing. First of all, it must be ensured that sufficient space is available at the installation site. The dimensions of the sampling module 4 are somewhat flexible and can be adjusted for specific requirements, but a rough indication is that a floor space of approximately 1 m2 and a height of approximately 2 m is needed. This allows sufficient space for the separation chamber 6, valves 8, 10, instrumentation 12, 14, 38 and T-junctions joining the valves 8, 10 to the pipeline 18. The design relies on a vertical spacing between the inlet and outlet and the pipe routing in and out of the multiphase flow meter 2 must therefore allow for vertical installation of sampling module 4, i.e. the outlet pipe should be routed above the inlet pipe.

Figure 4A:
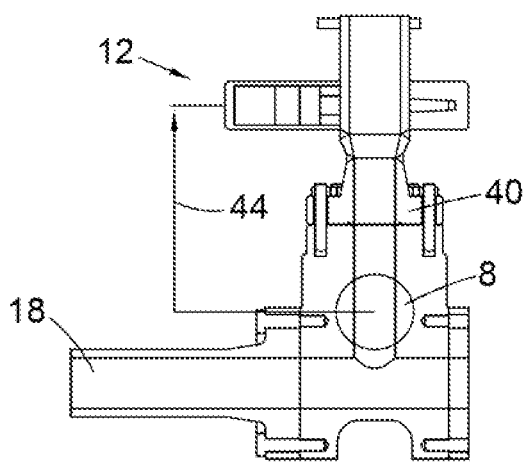
FIG. 4a shows an interface between the lower valve and the separation chamber of FIG. 1.

In the current example the separation chamber 6 includes a straight pipeline section with 3" diameter and a height of 1 m between connections to valve housing flanges 40. The total distance between the closing planes of the lower valve 8 and upper valve 10 is 1.36 m and this is the total vertical extent of the separation chamber 6. This gives a sample volume of approximately 6.2 liters. As is observed in FIG. 1, and also with reference to FIGS. 4a and 4b below, the valves 8, 10 make up a significant part of the height of the sampling module 4.

A MEG injection line and regulator, which would be used for the MEG injection mentioned above, are not included in the current drawings. MEG lines with relatively small diameter can easily be applied, such that the complexity and overall size of the module does not increase significantly. As discussed further below, it may also be possible to avoid use of MEG completely.

The diameter of the sampling module 4 is a compromise between several factors. The most important requirements for the module 4 are that sufficient volumes of all phases of the flow are sampled and that there are no left-overs from previous sampling within the module. This implies a rather large diameter for the separation chamber 6 and an absence of internal restrictions. Further, the separation chamber 6 should be filled within a reasonable time. Thus, the flow rate must be sufficient high and the volume of the separation chamber 6 must not be too large. A high flow rate will also help to remove possible wall deposits from the chamber. The size of the valves 8, 10 depend strongly on the pipe diameter, and the diameter should therefore be 4" or preferably less.

Based on this it is found that a 3" pipe section is a reasonable compromise. This allows a significant flow rate and acceptable filling time for typical flow rates, and a reasonable compact sampling module 4. The dimensions of the 3" valve applied in the concept illustration in FIG. 1 are based on modification of an existing compact 4" valve. In the drawings it is assumed that the 3" version will have a face-to-face length of approximately 80% of the 4" version.

The minimum height of the module is estimated from sensor requirements related to minimum oil and water layer thicknesses. The restricting instrument in this example is the gamma densitometer, which is shown in more detail in FIG. 2. The gamma source 24 (or 28) projects gamma radiation through the sample fluid in the separation chamber 6 to the gamma detector 26 (or 30). This type of sensor requires a fluid thickness of at least 5 cm for the fluid to be well characterized. Since there is some uncertainty in the positioning of the layer (which is controlled by the valves 8, 10), then some additional margin should be allowed (e.g. a thickness of 10 cm). It is reasonable to assume that water and oil are well mixed in the liquid sample, and the layer thickness for oil and water can then be calculated from the WLR and the height of the separation chamber 6:

Gamma densitometers are used to determine the linear attenuation coefficients of the various phases. The detector system can be similar to that found in multiphase flow meters. It is assumed that 137Cs sources with a gamma ray energy of 661.5 keV and scintillation detectors are used. This is in line with the gamma densitometers used in various known multiphase flow meters and matching the sensor in the sampling module 4 with that of the flow meter 2 allows for readings directly comparable to those in the multiphase flow meter 2. Geometry effects and the attenuation in pipe walls, detector housing, source holder can be eliminated from the equations through calibration with the detector system mounted on the multiphase flow meter 2. At the 137Cs gamma ray energy, the attenuation of the radiation ("the loss of gamma rays") in the process fluid is practically proportional to the density of the fluid, and the density is found from measurement of the linear attenuation coefficient.

To achieve the best possible uncertainty level for the gamma system, it may be advantageous to weld the source holder and the detector housing to the spool piece. Alternatively, a very strict fixture arrangement must be made to avoid any geometrical misalignment caused by vibrations etc. A flat surface for bolts directly into the body of the spool is one example of such an arrangement.

Figure 3:
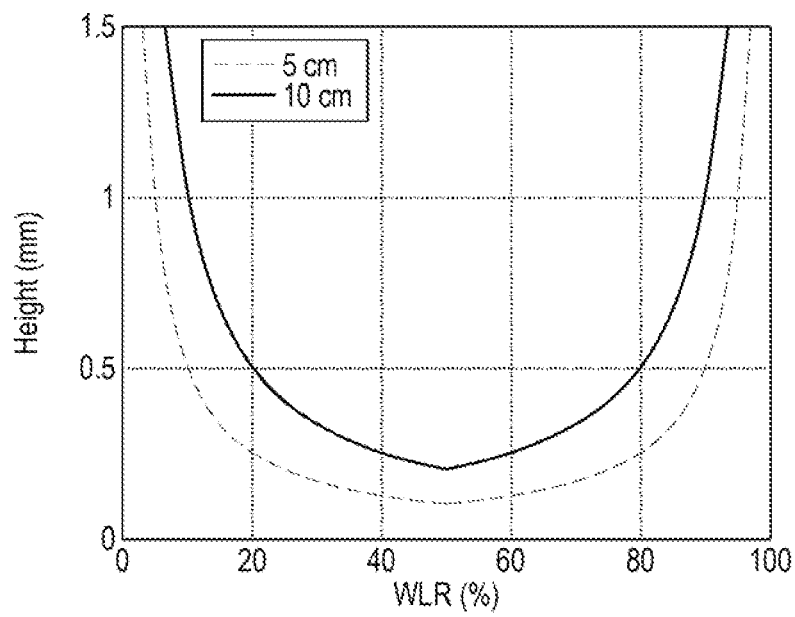
FIG. 3 is a graph showing the relationship between water-liquid ratio and a required height of the separation chamber.

In FIG. 3, the minimum required heights of the separation chamber 6 corresponding to layer thicknesses of 5 and 10 cm are shown for various WLR. As an example, the oil layer will be 10 cm or more in a 0.5 m long separation chamber 6 as long as WLR is less than 80%. A separation chamber 6 of greater height, e.g. 1 m, can deal with a greater range of WLR and/or allow for a narrower separation chamber 6.

The maximum height of the sampling module 4 is given by mechanical restrictions at the installation location, which may be a subsea flow control module. In the current design, a spacing of 1.66 m between the centers of the horizontal flow pipelines 18 is assumed. This is based on a 1 m height for the separation chamber 6 with the remaining 0.66 m assigned to the valves 8, 10 and associated housings.

The material of the separation chamber 6 may be stainless steel (super duplex). An alternative implementation is to coat the separation chamber 6 with a suitable material, or have an inner liner or pipe of a different material. It is known that the risk of corrosion, hydrate formation, scale and other deposits is much lower for plastic or coated pipes than for steel pipes. In addition, non-conductive inner pipeline will allow a wider range of electromagnetic sensors or sensor arrays to be installed. An inner pipe or window made in another material than steel will also allow use of multi-energy gamma ray sensors. The main reason for applying MEG in the sampling module 4 is to avoid deposition and fouling on the inner wall. Since the complexity of increases by having a dedicated MEG line, there are advantages if it is possible to completely avoid MEG such that the separation chamber 6 is filled with process fluid (or gas) when the system is idle. This might be possible if the inner wall of the separation chamber 6 is coated or have an inner liner or pipe.

Another concern is that the temperature may fall drastically when the system is idle, and therefore increase the risk for hydrate formation even with a coated interior of the chamber 6. This can be avoided by flushing the system with process flow when the temperature falls towards the hydrate equilibrium temperature, or to insulate the separation chamber, or to install the separator chamber close to the multiphase meter and within the same insulation such that the separator chamber is heated by the multiphase meter.

It is important that the temperature within the separation chamber 6 is kept close to the operating conditions of the multiphase flow meter 2 during analysis. If the separation time is long, there is a small risk that the temperature will fall significantly. This can be avoided by applying heating at the separation chamber 6 in order to keep the temperature close to the multiphase flow meter temperature. An electric heater may be used. This heating does not have to be used continuously, but may be turned on when temperature drops significantly. Heating could also be used when the sampling module 4 is not in use in order to avoid hydrate formation at lower temperatures, An alternative to heater could be to insulate the separation chamber, and also to install the separator chamber close to the multiphase meter and within the same insulation such that the separator chamber is heated by the multiphase meter. The design of FIG. 1 is based on a modular design where the separation chamber 6 and valves are assembled with mounting screws at their flanges 40 as shown in close up view in FIG. 4a. A drawback of this design is that the flanges 40 and need for access for the mounting screws takes up a significant vertical space. Thus, there will be a significant height 42 between the closing plane of the valves and the measurement plane. With the use of separate valve housings with flanged connections 40 to the central part of the separation chamber 6 then this height may be 430 mm with the dimensions and pipe sizes discussed above. This is not a problem for the upper sensor set 14 where the liquid levels can be controlled by direct feedback from the sensors 14 to the actuators 20 that control the upper valve 10. However, this distance means that water has to accumulate to a level higher than 430 mm before it can be characterized by the lower sensor set 12. For a design with a distance of 1.36 m between the valves' closing planes, this means that the water-oil interface will be below the lower sensor set for liquids with WLR lower than approximately 30% after separation. This is not necessarily problematic where the sampling module 4 is used in conjunction with some types of multiphase flow meter 2 for oil and gas as in that context it may not be important to characterize water when the WLR is low. Nevertheless, for other applications of the sampling module 4 it may be vital to also characterize water.

Figure 4B:
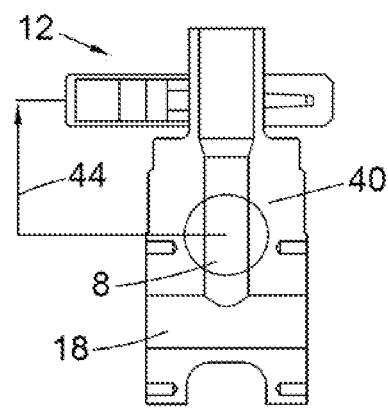
FIG. 4b shows an alternative arrangement for the interface between the valve and the separation chamber.

Thus, to reduce the height 42 between the valve closing plane and the sensing plane for the lower sensor set 12 then an alternative design is to form the separation chamber 6 and the valve housing as one integrated part 44 as illustrated in FIG. 4b. Such an integrated part may be fabricated by casting, machining and/or welding. With this adaptation then the lower sensor set 12 may be placed close to the valve, for example approximately 250 mm from the valves' closing plane, corresponding to a WLR of approximately 15% if the module is completely filled with a representative process liquid.

As discussed above, it can be challenging to characterize water if the water-liquid-ratio is low since the distance from the lower valve ball to the lower sensor set 12 is long. An alternative way of handling this is to modify the control system 38 slightly as described in the following. After the liquid has been sampled and separated into water and oil phases, the upper valve 10 is reopened such that oil at upper part of the separation chamber 6 is replaced by new process liquid. When the valve 10 is closed again then water will separate and fall to the lower part of the chamber 6 and move the water-oil interface up. It may be required to re-open the upper valve 10 several times in order to accumulate enough water. This is controlled by giving a control signal from the lower sensor set 12 when water continuous liquid is sensed. Alternatively, an additional sensor or sensors may be provided for detecting the fluid interfaces (i.e. level detectors, see further discussion below), which can be used as input to the controller 38. Level detectors will also be beneficial for the algorithm that controls the closing and opening of valves, in particular if refilling is needed to fine-adjust the liquid levels.

The challenge regarding characterization of small water volumes can also be solved by changing the geometry of the separation chamber 6 such that the diameter in the lower part of the separation chamber 6 is smaller than at the upper part. This geometry ensures that the water volume occupies a much larger vertical distance than in the original concept. The challenge with this design is that the diameter of the lower part of the sampling module 4 is small. Further on, the dimensions of the upper and lower valve will be different unless the dimensions are reduced again at the top.

The liquid sampled just after closing the valves simultaneously might have a representative WLR. Thus, by measuring the water-oil interface (and possible the gas-oil interface if there is remaining gas in the chamber) after separation, the WLR can be calculated. This can be used for redundancy and quality assurance of the multiphase flow meter 2.

The multiphase flow meter 2 input parameters are measured with gamma densitometers and permittivity/conductivity sensors. Additional information of relevance can be extracted by adding additional sensors to the separation chamber 6.

Some examples of additional information and relevant sensor technologies are discussed in the following. As mentioned above, it may be beneficial to include level detectors in the separation chamber 6. There are several potential methods that can be used for measuring interface levels, including electromagnetic, gamma, and ultrasonic technologies. The separation time and water distribution within the oil layer can be measured by implementing an array of permittivity sensors within the separation chamber 6. Such an array can also be used for level detection. Ultrasonic transducers can be included to measure the velocity of sound. This can be applied for instance for density measurements and calorific value of hydrocarbon gas. By combining gamma densitometer and permittivity measurements of water, it may be possible to extract information about ion composition, and thereby identify whether the water is formation water or sea water. The reliability of multiphase flow meters 2 can be improved if viscosity also is provided as an input parameter and therefore a viscosity sensor may be included.

The benefit from the sampling module 4 depends on accurate measurements of the attenuation constants and permittivities of the three phases. The random errors of the sensors 12, 14 can be evaluated experimentally, but it is harder to quantify systematic errors in the sensor systems 12, 14. Such systematic errors can occur due to drift in electronics, movement and wearing of sensors, deposits on the sensors etc. It is therefore important to be able to calibrate the sensors towards known references, or at least to check the quality of the measured data in some way (i.e. sensor validation).

Drift and other systematic errors in the electronic units can be calibrated by measuring included internal reference components. Another way to calibrate the sensors is to fill the separation chamber 6 with well-defined fluids that have properties close to those of gas, oil and water. This is difficult to achieve, as such fluids are not available subsea. MEG, methanol or similar liquids are, however, available for hydrate control at most subsea stations. MEG is typically mixed with water, and can be used as reference fluid for attenuation constant and permittivity calibration if the water fraction is known.

Sensor validation or quality checking can be done by exploiting redundancy in measurements, for instance by measuring the same fluid properties with different sensor technologies. This can either be done by adding additional sensors, and/or by taking advantage of redundancy between permittivity and gamma densitometer measurements.

The lower sensor set 12 consists of a gamma densitometer that measures attenuation constants and a permittivity/conductivity sensor 34 that measures water dielectric constant and conductivity. Water is a well-defined fluid, and the relation between density (and also attenuation constant) and salinity is known for typical ion compositions. Also, the dielectric constant and conductivity of water are known for typical ion compositions. Thus, a validation of the measured water parameters can be done by comparing the three measured parameters (attenuation constant, dielectric constant and conductivity) towards each other. For instance, the density measurements provided by the gamma densitometer can be compared with conductivity measurements form the permittivity sensor. If the measured values do not agree with known valves, then one of the sensors is probably failing. If the dielectric constant measurements correspond with the conductivity measurements, it is probably the gamma densitometer that is failing. If dielectric constant and conductivity measurement values do not agree, it is the permittivity/conductivity sensor 34 that is failing.

The upper sensor set 14 is used to measure gas and oil properties. Correlations between density and permittivity of gas and crude oil have been published and these may be applied for quality checking of the gamma densitometer and the permittivity sensor against each other. Use of redundant sensors for measuring fluid properties is however seen as a more reliable option. Ultrasonic sensors can be used to measure gas and oil density, while for instance capacitive sensors or microwave resonance methods are well suited to measure gas and oil permittivities.

In addition to validating the sensors 12, 14 against each other or against redundant sensors, they may also be checked against multiphase flow meter 2 meter and PVT calculations. This comparison should of course not be used to correct sensor readings, but may be used as in an overall data quality algorithm.

The invention claimed is:

1. A sampling module for mounting in a pipeline with a multiphase flow meter and for receiving multiphase fluid from the pipeline, the sampling module comprising:
    a separation chamber for receiving and separating a sample volume of fluid from the multiphase fluid, the separation chamber having a vertical extent when in use;
    a lower valve for opening and closing a lower fluid path between a lower end of the separation chamber and the pipeline;
    an upper valve for opening and closing an upper fluid path between an upper end of the separation chamber and the pipeline;
    a lower sensor for measuring fluid properties of the fluid in a lower part of the separation chamber and/or an upper sensor for measuring fluid properties of the fluid in an upper part of the separation chamber; and
    a controller for opening and closing the lower valve and the upper valve by each of: opening and closing both the lower valve and the upper valve together; opening and closing the upper valve while the lower valve remains closed; and opening and closing the lower valve while the upper valve remains closed,
    wherein the controller is configured to:
    control sequence and timing of valve opening and closing operations;
    allow for a settling time after both the lower valve and the upper valve are closed so that the sample volume can separate within the vertical extent of the separation chamber; and
    vary the settling time depending on readings from the lower sensor and/or the upper sensor.

2. The sampling module of claim 1, wherein the pipeline is an oil and gas pipeline and the multiphase fluid is from an oil and gas installation.

3. The sampling module of claim 1, wherein the sampling module is a subsea sampling module and the pipeline is a subsea pipeline.

4. The sampling module of claim 1, wherein, in order to obtain the sample volume of fluid as a complete mixture, the sampling module is configured to: (i) open both the lower valve and the upper valve so that the multiphase fluid from the pipeline flows through the sampling module; and (ii) close both the lower valve and the upper valve to retain the sample volume of fluid in the separation chamber.

5. The sampling module of claim 1, wherein, in order to obtain the sample volume of fluid as just heavier phases of the multiphase fluid, the sampling module is configured to: (i) open the upper valve while the lower valve remains closed so that heavier parts of the multiphase fluid enter the sample volume of fluid while displacing any lighter parts; and (ii) close the upper valve to retain the sample volume of fluid as just the heavier phases of the multiphase fluid in the separation chamber.

6. The sampling module of claim 1, wherein in order to obtain the sample volume of fluid as just lighter phases of the multiphase fluid, the sampling module is configured to: (i) open the lower valve while the upper valve remains closed so that lighter parts of the multiphase fluid enter the sample volume of fluid while displacing any heavier parts; and (ii) close the lower valve to retain the sample volume of fluid as just the lighter phases of the multiphase fluid in the separation chamber.

7. The sampling module of claim 1, wherein the controller is further configured to: (i) allow for a fill time to fill the separation chamber before the separation chamber is sealed for settling of the sample volume of fluid; and (ii) vary the fill time depending on readings from the lower sensor and/or the upper sensor.

8. The sampling module of claim 1, further comprising a temperature sensor and a pressure sensor.

9. The sampling module of claim 1, further comprising a connection to a source of hydrate blocker for the separation chamber before the separation chamber is closed off in periods when the sampling module is not in use.

10. The sampling module of claim 1, further comprising a heater for heating the separation chamber and/or insulation for retaining heat within the separation chamber.

11. A multiphase flow meter apparatus comprising:
    the sampling module of claim 1; and
    the multiphase flow meter for monitoring fluid flow in the pipeline.

12. The multiphase flow meter apparatus of claim 11, further comprising a system for adjustment of the multiphase flow meter based on measurements from the lower sensor and/or the upper sensor.

13. The multiphase flow meter apparatus of claim 11, wherein the sampling module is configured to be coupled to the pipeline in parallel with the multiphase flow meter.

14. The multiphase flow meter apparatus of claim 11, wherein the vertical extent of the separation chamber is in parallel with a vertical extent of the multiphase flow meter.

15. The multiphase flow meter apparatus of claim 11, wherein the sampling module is in an insulated volume along with the multiphase flow meter so that heat from the multiphase flow meter can be transferred to the sampling module.

16. A non-transitory computer readable storage medium having stored thereon a program implemented by the sampling module of claim 1, the program causing the sampling module to perform steps comprising:
    opening and closing the lower valve in order to allow fluid flow along the lower fluid path and/or opening and closing the upper valve in order to allow fluid flow along the upper fluid path;
    obtaining the sample volume of fluid from the multiphase fluid in the separation chamber;
    closing the lower valve and the upper valve;
    holding the sample volume of fluid within the separation chamber to allow the fluid to settle and separate; and
    measuring fluid properties of the fluid settled in the lower part of the separation chamber using the lower sensor and/or measuring fluid properties of the fluid settled in the upper part of the separation chamber using the upper sensor.

19

17. A method for obtaining input parameters for a multiphase flow meter, the method using a sampling module for mounting in a pipeline with the multiphase flow meter and for receiving multiphase fluid from the pipeline, wherein the sample module includes a lower valve, an upper valve, and a controller for opening and closing the lower valve and the upper valve by each of: opening and closing both the lower valve and the upper valve together; opening and closing the upper valve while the lower valve remains closed; and opening and closing the lower valve while the upper valve remains closed, and wherein the controller is configured to control sequence and timing of valve opening and closing operations, allow for a settling time after both the lower valve and the upper valve are closed so that a sample volume of fluid from the multiphase fluid can separate within a vertical extent of a separation chamber of the sampling module, and vary the settling time depending on readings from a lower sensor and/or an upper sensor, the method comprising:

opening and closing the lower valve in order to allow fluid flow along a lower fluid path between a lower end of the separation chamber and the pipeline and/or opening and closing the upper valve in order to allow fluid flow along an upper fluid path between an upper end of the separation chamber and the pipeline;

obtaining the sample volume of fluid in the separation chamber which has the vertical extent when in use;

closing the lower valve and the upper valve;

holding the sample volume of fluid within the separation chamber to allow the fluid to settle and separate; and measuring fluid properties of the fluid settled in a lower part of the separation chamber using the lower sensor which is in the lower part of the separation chamber and/or measuring fluid properties of the fluid settled in an upper part of the separation chamber using the upper sensor which is in the upper part of the separation chamber.

18. A multiphase flow meter apparatus comprising:

a sampling module for mounting in a pipeline with a multiphase flow meter and for receiving multiphase fluid from the pipeline;

the multiphase flow meter being for monitoring fluid flow in the pipeline, the sampling module comprising:

a separation chamber for receiving and separating a sample volume of fluid from the multiphase fluid, the separation chamber having a vertical extent when in use;

a lower valve for opening and closing a lower fluid path between a lower end of the separation chamber and the pipeline;

an upper valve for opening and closing an upper fluid path between an upper end of the separation chamber and the pipeline;

a lower sensor for measuring fluid properties of the fluid in a lower part of the separation chamber and/or an upper sensor for measuring fluid properties of the fluid in an upper part of the separation chamber; and a controller for opening and closing the lower valve and the upper valve by each of: opening and closing both the lower valve and the upper valve together; opening and closing the upper valve while the lower valve remains closed; and opening and closing the lower valve while the upper valve remains closed,

20 wherein the sampling module is in an insulated volume along with the multiphase flow meter so that heat from the multiphase flow meter can be transferred to the sampling module.

19. The multiphase flow meter apparatus of claim 18, wherein the pipeline is an oil and gas pipeline and the multiphase fluid is from an oil and gas installation.

20. The multiphase flow meter apparatus of claim 18, wherein the sampling module is a subsea sampling module and the pipeline is a subsea pipeline.

21. The multiphase flow meter apparatus of claim 18, wherein, in order to obtain the sample volume of fluid as a complete mixture, the sampling module is configured to: (i) open both the lower valve and the upper valve so that the multiphase fluid from the pipeline flows through the sampling module; and (ii) close both the lower valve and the upper valve to retain the sample volume of fluid in the separation chamber.

22. The multiphase flow meter apparatus of claim 18, wherein, in order to obtain the sample volume of fluid as just heavier phases of the multiphase fluid, the sampling module is configured to: (i) open the upper valve while the lower valve remains closed so that heavier parts of the multiphase fluid enter the sample volume of fluid while displacing any lighter parts; and (ii) close the upper valve to retain the sample volume of fluid as just the heavier phases of the multiphase fluid in the separation chamber.

23. The multiphase flow meter apparatus of claim 18, wherein in order to obtain the sample volume of fluid as just lighter phases of the multiphase fluid, the sampling module is configured to: (i) open the lower valve while the upper valve remains closed so that lighter parts of the multiphase fluid enter the sample volume displacing any heavier parts; and (ii) close the lower valve to retain the sample volume of fluid as just the lighter phases of the multiphase fluid in the separation chamber.

24. The multiphase flow meter apparatus of claim 18, wherein the controller is configured to control sequence and timing of valve opening and closing operations.

25. The multiphase flow meter apparatus of claim 24, wherein the controller is further configured to: (i) allow for a fill time to fill the separation chamber before the separation chamber is sealed for settling of the sample volume of fluid; and (ii) vary the fill time depending on readings from the lower sensor and/or the upper sensor.

26. The multiphase flow meter apparatus of claim 24, wherein the controller is further configured to: (i) allow for a settling time after both the lower valve and the upper valve are closed so that the sample volume can separate within the vertical extent of the separation chamber; and (ii) vary the settling time depending on readings from the lower sensor and/or the upper sensor.

27. The multiphase flow meter apparatus of claim 18, further comprising a temperature sensor and a pressure sensor.

28. The multiphase flow meter apparatus of claim 18, further comprising a connection to a source of hydrate blocker for the separation chamber before the separation chamber is closed off in periods when the sampling module is not in use.

29. The multiphase flow meter apparatus of claim 18, further comprising a heater for heating the separation chamber and/or insulation for retaining heat within the separation chamber.

30. The multiphase flow meter apparatus of claim 18, further comprising a system for adjustment of the multiphase flow meter based on measurements from the lower sensor and/or the upper sensor.

31. The multiphase flow meter apparatus of claim 18, wherein the sampling module is configured to be coupled to the pipeline in parallel with the multiphase flow meter.

32. The multiphase flow meter apparatus of claim 18, wherein the vertical extent of the separation chamber is in parallel with a vertical extent of the multiphase flow meter.

33. A non-transitory computer readable storage medium having stored there on a program implemented by the multiphase flow meter apparatus of claim 18, the program causing the sampling module to perform steps comprising:
  opening and closing the lower valve in order to allow fluid flow along a lower fluid path and/or opening and closing the upper valve in order to allow fluid flow along the upper fluid path;
  obtaining the sample volume of fluid from the multiphase fluid in the separation chamber;
  closing the lower valve and the upper valve;
  holding the sample volume of fluid within the separation chamber to allow the fluid to settle and separate; and
  measuring fluid properties of the fluid settled in the lower part of the separation chamber using the lower sensor and/or measuring fluid properties of the fluid settled in the upper part of the separation chamber using the upper sensor.

34. A method for obtaining input parameters for a multiphase flow meter, the method using a sampling module for mounting in a pipeline with the multiphase flow meter and for receiving multiphase fluid from the pipeline, wherein the sample module includes a lower valve, an upper valve, and a controller for opening and closing the lower valve and the upper valve by each of: opening and closing both the lower valve and the upper valve together; opening and closing the upper valve while the lower valve remains closed; and opening and closing the lower valve while the upper valve remains closed, and wherein the sampling module is in an insulated volume along with the multiphase flow meter so that heat from the multiphase flow meter can be transferred to the sampling module, the method comprising:
  opening and closing the lower valve in order to allow fluid flow along a lower fluid path between a lower end of a separation chamber of the sampling module and the pipeline and/or opening and closing the upper valve in order to allow fluid flow along an upper fluid path between an upper end of the separation chamber and the pipeline;
  obtaining a sample volume of fluid from the multiphase fluid in the separation chamber which has a vertical extent when in use;
  closing the lower valve and the upper valve;
  holding the sample volume of fluid within the separation chamber to allow the fluid to settle and separate; and
  measuring fluid properties of the fluid settled in a lower part of the separation chamber using a lower sensor in the lower part of the separation chamber and/or measuring fluid properties of the fluid settled in an upper part of the separation chamber using an upper sensor in the upper part of the separation chamber.

* * * * *